(12) United States Patent
Saint Victor et al.

(10) Patent No.: US 9,909,086 B2
(45) Date of Patent: Mar. 6, 2018

(54) GREEN GLYCINE BETAINE DERIVATIVE COMPOUNDS AND COMPOSITIONS CONTAINING SAME

(71) Applicants: Marie-Esther Saint Victor, Glencoe, IL (US); Thierry Benvegnu, Rennes (FR); Hakima-Fatima Azira, Le Perreux-sur-Marne (FR)

(72) Inventors: Marie-Esther Saint Victor, Glencoe, IL (US); Thierry Benvegnu, Rennes (FR); Hakima-Fatima Azira, Le Perreux-sur-Marne (FR)

(*) Notice: Subject to any disclaimer, the term of this patent is extended or adjusted under 35 U.S.C. 154(b) by 0 days.

(21) Appl. No.: 14/739,925

(22) Filed: Jun. 15, 2015

(65) Prior Publication Data
US 2015/0275138 A1 Oct. 1, 2015

Related U.S. Application Data

(63) Continuation of application No. 13/495,431, filed on Jun. 13, 2012, now abandoned.

(51) Int. Cl.
| | |
|---|---|
| C11D 1/90 | (2006.01) |
| A01N 25/30 | (2006.01) |
| A01N 37/44 | (2006.01) |
| C11D 3/48 | (2006.01) |
| C11D 3/22 | (2006.01) |

(52) U.S. Cl.
CPC ............. *C11D 1/90* (2013.01); *A01N 25/30* (2013.01); *A01N 37/44* (2013.01); *C11D 3/222* (2013.01); *C11D 3/48* (2013.01)

(58) Field of Classification Search
CPC .... C11D 1/90; C11D 1/92; C11D 3/48; C11D 3/222; A01N 25/30; A01N 37/44
USPC ................................... 510/405, 470
See application file for complete search history.

(56) References Cited

U.S. PATENT DOCUMENTS

| | | | |
|---|---|---|---|
| 2,888,383 A | 5/1959 | Byrne | |
| 3,578,499 A | 5/1971 | Crotty et al. | |
| 4,020,100 A | 4/1977 | Evans et al. | |
| 4,041,205 A | 8/1977 | Compa et al. | |
| 4,076,743 A | 2/1978 | Koch et al. | |
| 4,080,100 A | 3/1978 | McNeese | |
| 4,231,890 A | 11/1980 | Yagi et al. | |
| 4,252,656 A | 2/1981 | Liebowitz et al. | |
| 4,370,272 A | 1/1983 | Wechsler et al. | |
| 4,375,421 A | 3/1983 | Rubin et al. | |
| 4,690,818 A * | 9/1987 | Puchalski, Jr. ........ | A61K 8/042 424/70.14 |
| 4,790,978 A | 12/1988 | Allenmark et al. | |
| 4,839,077 A | 6/1989 | Cramer et al. | |
| 4,874,789 A | 10/1989 | Smith et al. | |
| 4,936,864 A | 6/1990 | Fikentscher et al. | |
| 4,943,612 A | 7/1990 | Morita et al. | |
| 5,109,127 A | 4/1992 | Sekiguchi et al. | |
| 5,190,747 A | 3/1993 | Sekiguchi et al. | |
| 5,213,792 A | 5/1993 | Grundmann et al. | |
| 5,429,755 A | 7/1995 | Ilardi et al. | |
| 5,472,455 A | 12/1995 | Mehreteab et al. | |
| 5,527,477 A | 6/1996 | Ilardi et al. | |
| 5,607,691 A | 3/1997 | Hale et al. | |
| 5,663,138 A | 9/1997 | Ilardi et al. | |
| 5,703,036 A | 12/1997 | Iakovides | |
| 5,851,982 A | 12/1998 | Sakata et al. | |
| 5,858,960 A | 1/1999 | Conroy et al. | |
| 5,958,870 A | 9/1999 | Declercq et al. | |
| 5,961,999 A * | 10/1999 | Bimczok .................. | 424/401 |
| 6,207,629 B1 | 3/2001 | Gonzalez et al. | |
| 6,274,539 B1 | 8/2001 | Kaecher et al. | |
| 6,280,883 B1 | 8/2001 | Lamanna et al. | |
| 6,294,104 B1 | 9/2001 | Ilves et al. | |
| 6,336,977 B1 | 1/2002 | Menke et al. | |
| 6,346,259 B1 | 2/2002 | Terasaki et al. | |
| 6,346,506 B1 | 2/2002 | Julemont | |
| 6,380,152 B1 | 4/2002 | Julemont et al. | |
| 6,383,997 B1 | 5/2002 | McManus | |
| 6,384,266 B1 | 5/2002 | Farone et al. | |
| 6,410,499 B1 | 6/2002 | Julemont et al. | |
| 6,429,182 B1 | 8/2002 | Julemont et al. | |
| 6,429,183 B1 | 8/2002 | Leonard et al. | |
| 6,432,896 B1 | 8/2002 | Inaba et al. | |
| 6,436,892 B1 | 8/2002 | Leonard et al. | |
| 6,486,333 B1 | 11/2002 | Murayama et al. | |

(Continued)

FOREIGN PATENT DOCUMENTS

| | | |
|---|---|---|
| CN | 101987076 | 3/2011 |
| CN | 102008409 | 4/2011 |

(Continued)

OTHER PUBLICATIONS

Estrine et al. (WO 2005/121294 A1; cited on IDS, D11 on ISR), machine translation (from EPO, Jul. 30, 2015), 53 pages.*

(Continued)

*Primary Examiner* — Ernst V Arnold

(57) ABSTRACT

Multifunctional green and antimicrobial compositions are described containing cationic glycine betaine esters and/or cationic glycine betaine amides. Particular glycine betaine esters and amides are alkyl(ene) betainate methane sulfonates and betainyl amino alkyl(ene) methane sulfonates. The glycine betaine components are cationic, have a hydrophobic group attached to a carboxylate group through an ester or amide linkage, and are derived from a natural source, such as sugar beets. The glycine betaine esters and amides serve as cationic surfactants which have effective antimicrobial activity. The surfactant compositions are effective as crude mixtures or semi-purified mixtures or purified surfactant compounds of glycine betaine components. The addition of sodium chloride or potassium chloride or magnesium chloride or natural gum or polysaccharide to compositions containing the cationic glycine betaine ester and/or glycine betaine amide derivatives serves to thicken or gel the composition.

25 Claims, No Drawings

(56) References Cited

U.S. PATENT DOCUMENTS

| | | |
|---|---|---|
| 6,495,508 B1 | 12/2002 | Leonard et al. |
| 6,518,229 B2 | 2/2003 | Tashjian et al. |
| 6,551,971 B2 | 4/2003 | Inaba et al. |
| 6,586,639 B2 | 7/2003 | Murayama et al. |
| 6,617,296 B1 | 9/2003 | Connors et al. |
| 6,624,126 B1 * | 9/2003 | Kasuga .............. A61K 8/23 510/130 |
| 6,639,120 B1 | 10/2003 | Wallajapet et al. |
| 6,641,826 B2 | 11/2003 | Durden |
| 6,649,580 B2 | 11/2003 | Aszman et al. |
| 6,667,287 B2 | 12/2003 | Aszman et al. |
| 6,683,033 B2 | 1/2004 | Gonzalez et al. |
| 6,815,406 B1 | 11/2004 | Szewczyk |
| 6,897,263 B2 | 5/2005 | Hell et al. |
| 7,022,661 B2 | 4/2006 | Behler et al. |
| 7,053,033 B2 | 5/2006 | Scheper |
| 7,056,878 B2 | 6/2006 | Fender et al. |
| 7,087,567 B2 | 8/2006 | Connors et al. |
| 7,183,239 B2 | 2/2007 | Smith et al. |
| 7,202,199 B2 | 4/2007 | Shiloach et al. |
| 7,205,271 B2 | 4/2007 | Drzewinski et al. |
| 7,229,958 B2 | 6/2007 | Kohle et al. |
| 7,279,456 B2 | 10/2007 | Dufay et al. |
| 7,297,667 B2 | 11/2007 | Potechin et al. |
| 7,307,052 B2 | 12/2007 | Murthy et al. |
| 7,314,951 B2 | 1/2008 | Rivers et al. |
| 7,405,188 B2 | 7/2008 | Chen |
| 7,482,021 B1 | 1/2009 | Tison et al. |
| 7,501,390 B2 | 3/2009 | Yagi et al. |
| 7,517,582 B2 | 4/2009 | Amundson et al. |
| 7,591,272 B2 | 9/2009 | Dastbaz et al. |
| 7,597,954 B2 | 10/2009 | Amundson et al. |
| 7,605,096 B2 | 10/2009 | Tomarchio et al. |
| 7,608,573 B1 | 10/2009 | Scheuing et al. |
| 7,618,931 B1 | 11/2009 | Scheuing et al. |
| 7,635,672 B1 | 12/2009 | Dastbaz et al. |
| 7,662,225 B2 | 2/2010 | Antoine et al. |
| 7,718,595 B2 * | 5/2010 | Murphy ............. C11D 1/94 510/424 |
| 7,776,811 B2 | 8/2010 | Dilley et al. |
| 7,829,521 B2 * | 11/2010 | Antoine .............. A61K 8/44 427/138 |
| 7,928,053 B2 | 4/2011 | Hecht et al. |
| 7,981,856 B2 * | 7/2011 | Antoine .............. A61K 8/44 510/499 |
| 9,066,877 B2 | 6/2015 | Mintchev et al. |
| 2001/0006981 A1 | 7/2001 | Odds et al. |
| 2002/0151446 A1 * | 10/2002 | Piterski ............. A61K 8/442 510/130 |
| 2003/0108513 A1 | 6/2003 | Hell et al. |
| 2003/0114315 A1 | 6/2003 | Schwartz et al. |
| 2005/0079990 A1 | 4/2005 | Chan et al. |
| 2005/0217537 A1 | 10/2005 | Knipe |
| 2006/0100115 A1 | 5/2006 | Sakurai et al. |
| 2006/0163529 A1 | 7/2006 | Jokinen |
| 2006/0175298 A1 | 8/2006 | Zhao et al. |
| 2006/0196778 A1 | 9/2006 | Jia et al. |
| 2006/0246120 A1 | 11/2006 | Kelly et al. |
| 2006/0264349 A1 | 11/2006 | Connors et al. |
| 2007/0065475 A1 | 3/2007 | Elfersy |
| 2007/0197420 A1 * | 8/2007 | Antoine .............. A61K 8/44 510/499 |
| 2007/0202064 A1 | 8/2007 | Drzewinski et al. |
| 2007/0243321 A1 | 10/2007 | Antoine et al. |
| 2008/0035882 A1 | 2/2008 | Zhao et al. |
| 2008/0145426 A1 | 6/2008 | Amundson et al. |
| 2008/0167211 A1 | 7/2008 | Pivonka et al. |
| 2008/0251252 A1 | 10/2008 | Schwartz |
| 2009/0068255 A1 | 3/2009 | Yu et al. |
| 2009/0093388 A1 | 4/2009 | Yamawaki et al. |
| 2009/0155327 A1 | 6/2009 | Martin et al. |
| 2009/0291873 A1 | 11/2009 | Tamboli |
| 2010/0056416 A1 | 3/2010 | Scheuing et al. |
| 2010/0086576 A1 | 4/2010 | Myntti |
| 2010/0101605 A1 | 4/2010 | Saint Victor |
| 2010/0136079 A1 | 6/2010 | Kelly et al. |
| 2010/0144584 A1 | 6/2010 | Saint Victor |
| 2010/0160201 A1 | 6/2010 | Scheuing et al. |
| 2010/0183532 A1 | 7/2010 | Musa et al. |
| 2010/0189661 A1 | 7/2010 | Musa et al. |
| 2010/0234271 A1 | 9/2010 | Scheuing et al. |
| 2010/0272602 A1 | 10/2010 | Kelly et al. |
| 2010/0273694 A1 * | 10/2010 | Antoine .............. A61K 8/44 510/124 |
| 2011/0166105 A1 * | 7/2011 | Farng ............... A61K 47/18 514/75 |
| 2011/0168055 A1 | 7/2011 | Lommerts et al. |
| 2013/0291764 A1 | 11/2013 | Mehalebi et al. |

FOREIGN PATENT DOCUMENTS

| | | |
|---|---|---|
| DE | 35 27 974 | 2/1987 |
| DE | 249620 | 9/1987 |
| DE | 196 40 086 | 4/1998 |
| EP | 0 192 145 | 8/1986 |
| EP | 0 230 698 | 8/1987 |
| EP | 0 298 065 | 1/1989 |
| EP | 1 000 544 A1 | 5/2000 |
| EP | 1 016 650 | 7/2000 |
| FR | 2869912 | 11/2005 |
| GB | 2288186 | 10/1995 |
| JP | 2009-149573 | 7/2009 |
| WO | WO 97/40133 | 10/1997 |
| WO | WO-2005/121252 | 12/2005 |
| WO | WO-2005/121291 | 12/2005 |
| WO | WO-2005/121294 | 12/2005 |
| WO | WO-2009/113854 | 9/2009 |

OTHER PUBLICATIONS

Abstract for JP 58-157750 A (Sep. 19, 1983) entitled Production of Betain Ester Salt.

PCT/US2013/045352 International Search Report and Written Opinion dated Sep. 20, 2013.

* cited by examiner

GREEN GLYCINE BETAINE DERIVATIVE COMPOUNDS AND COMPOSITIONS CONTAINING SAME

BACKGROUND

Glycine betaine (GB) (Formula 1 below) is a natural and inexpensive product derived from sugar beet molasses and constitutes a prime raw material for the preparation of biodegradable and biocompatible surfactants. Sugar beet molasses contains 0.2 to 0.3% betaine which constitutes 27% of the weight of the molasses. GB is extracted from sugar beet molasses through a chromatography process with water as the eluent. GB is made of a quaternary trimethyl alkyl ammonium moiety and a carboxylate functional group and is considered as GRAS (generally regarded as safe).

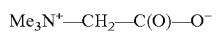

Formula 1: Chemical structure of glycine betaine.

Alkylbetaines and alkylamido betaines are the most widely used betaines. They are often made by the quaternization of a tertiary amine with chloroacetic acid. Typical betaine surfactants are illustrated in Formulas 2 and 3. The hydrophobic groups are attached to the ammonium group to provide zwitterionic or amphoteric surfactants. These surfactants exhibit both positive and negative charges due to the presence of ammonium and carboxylate groups, respectively. It is noted that the betaine group in commercial zwitterionic or amphoteric surfactants can be based on natural glycine betaine or synthesized glycine betaine.

Formula 2: Chemical Structures of Typical Betaine Surfactants.

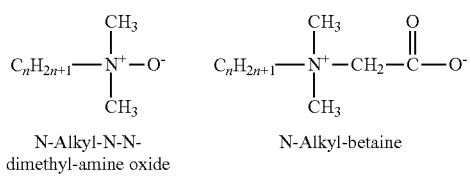

N-Alkyl-N-N-dimethyl-amine oxide     N-Alkyl-betaine

Formula 3: Cocamidopropyl Betaine or Lauramidopropyl Betaine or Cocamidopropyl Hydroxysultaine derived from coconut oil and glycine betaine.

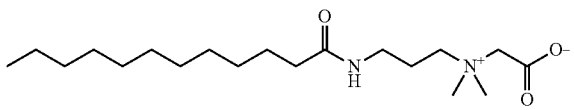

Betaine-type surfactants of the prior art are mostly amphoteric or zwitterionic betaines of the type shown in Formulas 2 and 3. These surfactants differ structurally and in their areas of use as compared to the GB derivative compounds of the invention which are cationic. Cationic betaine esters are known in the art, but such are synthesized and not based on natural sources.

For example, U.S. Pat. No. 6,384,266 B1 describes a method of synthesis of betaine esters. This patent does not disclose preparation of GB or derivatives of GB from natural sources. The method of synthesizing betaine esters is described therein as including (a) adding hydrochloric acid to a glycine betaine in a sufficient quantity to produce one mole of betaine hydrochloride for each mole of hydrochloric acid; (b) dissolving the betaine hydrochloride in water and adding concentrated hydrochloric acid to adjust the pH to 2; (c) chilling the solution for up to 24 hours, adding ethanol to facilitate formation of betaine hydrochloride crystals, filtering the betaine hydrochloride crystals, and drying the betaine hydrochloride crystals, (d) recycling the water-ethanol solution fraction for use in the next batch; (e) charging a reactor with a fatty acid derived alcohol and applying heat to liquefy the fatty acid derived alcohol, (f) adding the betaine hydrochloride crystals and an acid catalyst; (g) applying agitation and maintaining temperature; (h) reacting the mixture until esterification is complete, cooling the mixture, and adding a neutralization agent to neutralize the acid catalyst; (i) and purifying, crystallizing and drying the betaine ester product. The starting glycine betaine compound can be a by-product of sugar beet refining. The fatty acid derived alcohol is selected from a group containing 12 to 18 carbons and the esterification catalyst is sulfuric acid.

U.S. Pat. No. 7,662,225 B2 describes aqueous bitumen emulsions. The aqueous bitumen emulsions contain bitumen and a surfactant agent wherein the surfactant agent comprises at least one compound $X^-(CH_3)_3N^+$—$CH_2$—CO—Z—R, X being a sulphonate radical, R being a monovalent radical $C_{2n}H_{2(2n-m)+1}$ containing 2n atoms of carbon and m double bonds, with $9 \leq n \leq 11$, $0 \leq m \leq 3$ if $n=9$ and $0 \leq m \leq 1$ if $n>9$, and Z being selected from the group consisting of an atom of oxygen and a —NH— group.

U.S. Pat. No. 7,829,521 B2 describes cosmetic compositions comprising glycine betaine-type surfactants specifically for liquid soap, bath foam, shower gel or shampoo applications. The betaine surfactants comprise hydrocarbons chain length from C18 to C22.

FR 2 869 912 describes formulations based specifically on blends of pure ester or amide glycine betaine surfactants and commercial alkyl polyglycoside (APG) surfactants.

SUMMARY

Green (eco-friendly) and multifunctional cationic glycine betaine derivative compounds having surfactant and antimicrobial properties, in particular ester and amide derivatives, including alkyl(ene) betainate methane sulfonates and betainyl amino alkyl(ene) methane sulfonates, in semi-pure and crude mixtures and pure form, are described. Such compounds are includable in various household compositions to optimize solubilization, wetting, cleaning, emulsification of various oils and soils, and to provide effective antimicrobial properties. Further modification of compositions containing such derivatives is also provided through combination of the glycine betaine derivative(s) and sodium chloride to obtain thickening or gelling of the composition The application relates to sustainable, multifunctional, green (biodegradable), antimicrobial and disinfectant compositions for liquids, gels, aerosols and wipes comprising a minimum number of ingredients derived from natural sources. The compositions deliver excellent performance for multiple functions. The natural and green compositions comprise actives which provide both antimicrobial and surfactant properties, wherein such actives are obtained from renewable sources rather than being synthesized.

These actives are particularly useful in compositions for cleaning which comprise multifunctional and naturally derived novel surfactant structures that allow the compositions to deliver excellent cleaning performance and strong antimicrobial efficacy against both gram positive and gram negative bacteria, and fungi. These are effective over a wide pH range. Low pH compositions can perform with or without a buffer solution. These multi-functional surfactants also can act as adjuvants for active ingredients in pesticide and herbicide applications and as solubilizers and emulsifiers for fragrance and essential oils in air care applications. In the latter, the surfactants help to control the delivery of fragrances, perfume actives and oils in the form of microemulsions of these organic materials.

More particularly, the invention is directed to glycine betaine components, in particular, glycine betaine esters and glycine betaine amides in which a hydrophobic group is attached to a carboxylate group through an ester or amide linkage respectively. Examples of the surfactants are illustrated in Formula 4 below. The glycine betaine derivatives of the invention are cationic and positively charged rather than being zwitterionic or amphoteric as with prior art betaine surfactants described above. The introduction of an ester or amide linkage between the hydrophilic moiety (polar head group) and the hydrophobic backbone (alkyl or alkylene chain) improves biodegradability and confers unique solution and interfacial properties to the surfactants. In addition, glycine betaine ester or amide surfactants, such as alkyl betainate methane sulfonates or betainyl amino alkyl methane sulfonates, exhibit antimicrobial activities similar to quaternary ammonium salts (QUATs) against a broad spectrum of microorganisms.

Formula 4: Structure of alkyl betaine methane sulfonates and betainyl amino alkyl methane sulfonates.

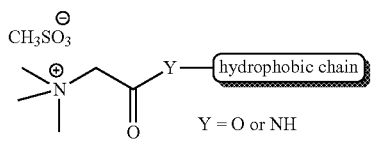

Y = O or NH

When Y is O=Alkyl Betainate Methane Sulfonate.
When Y is NH=Betainyl Amino Alkyl Methane Sulfonate.

The cationic GB ester and amide derivatives not only provide excellent antimicrobial efficacy, they play multiple functions in compositions, reducing the need for additional cleaning or wetting agents, contrary to conventional QUATs. Additionally, due to their ability to solubilize or emulsify a variety of oils, these surfactants allow solubilization and controlled release of actives, such as fragrances, herbicides and insecticides. Surface and interfacial properties of these GB ester and GB amide derivatives are comparable or better than conventional synthetic cationic surfactants, such as QUATs. In fact, they can be very effective adjuvants in agricultural formulations due to their very low surface and interfacial tensions that enable the formation of very fine particles in spray and aerosol compositions and adequate wetting of the substrates.

The ability of the GB-based surfactants to emulsify vegetable oils is demonstrated using a vegetable oil (sunflower oil) at neutral pH, stored and analyzed at 25° C. and at 37° C. Oil droplets with mean diameter of 220 to 260 nm and with narrow size distribution result. The emulsion ageing was also followed by photodensitometry, using a flat scanner. GB solutions exhibited good emulsifying ability at acid, neutral and basic pH against different types of oil phases, ranging from essential oils, mineral, vegetables to animal oils and soils as well as insoluble fragrances and pesticide oils.

Since the glycine betaine components of the invention are particularly useful in cleaning compositions, the invention will be described basically in relation to household compositions for simplicity of discussion. The properties described and exhibited will be comparable for other applications. GB esters and GB amide derivatives of the invention are cationic and positively charged. The compositions including these compounds exhibit strong efficacy against both gram positive and gram negative bacteria, have minimum inhibition concentration (MIC) values which tend to be lower than those of amphoteric betaines of the prior art, and exhibit a much lower Critical Micelle Concentration (CMC) and thus have better surfactant properties than conventional amphoteric surfactants.

The production of alkyl(ene) betainate methane sulfonates and betainyl amino alkyl(ene) methane sulfonates is also described. The production of these compounds is environmentally friendly since the process does not require a solvent and does not result in waste. These glycine betaine components are especially useful in crude mixtures as obtained during preparation, as well as are useful in semi-purified and purified mixtures.

As used herein the following terms are understood to mean: (1) "crude"—reaction product as formed, i.e., as is, and used without further treatment; (2) "semi-pure" or "semi-purified"—the reaction product formed is partly purified, i.e., residual glycine betaine and alkyl amine are stripped off; and (3) "pure" or "purified"—the reaction product formed is treated so as to contain no residual raw materials, and is 100% surfactant rich.

The preparation of and purification of alkyl betainate methane sulfonates (GB ester derivatives) follows a pathway for the esterification reaction of GB as follows:

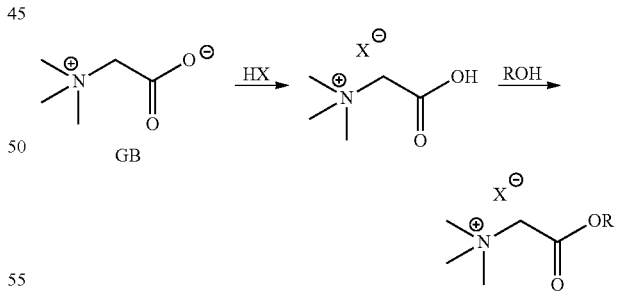

Acid-catalyzed esterification reaction between GB and fatty alcohols proceeds in one-step via the in situ protonation of the carboxylate function. Only environmentally friendly raw materials are used under solvent-free conditions, i.e., during reaction of compounds to form the GB ester derivatives of the invention, no compounds serving the function of a solvent are present.

The use of methane sulfonic acid (MSA), as acid for protonation of the carboxylate function is also beneficial in providing a green route to obtain GB esters. Being part of the natural sulfur cycle, MSA is considered natural and readily biodegradable. Indeed, MSA is an easy-to-handle liquid, often recyclable and less aggressive than common organic acids conventionally used such as hydrochloric, sulfuric or hydrofluoric acid. It is considered readily biodegradable, ultimately forming sulfates and carbon dioxide. MSA, in fact is considered to be a natural product and part of the natural sulfur cycle.

An example of the one-step process of preparing of GB esters, using MSA as the catalyst is illustrated for octadecyl betainate methane sulfonate ($C_{18:0}$ stearic GB ester) and (Z)-octadec-9-enyl betainate methane sulfonate [GB oleic ester ($C_{18:1}$)] as follows:

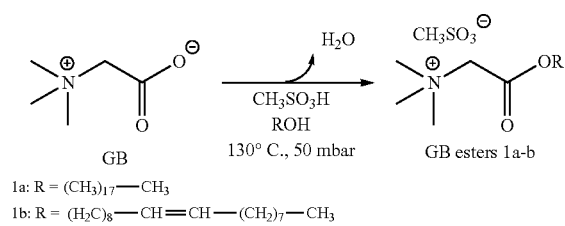

1a: R = $(CH_3)_{17}$—$CH_3$
1b: R = $(H_2C)_8$—CH═CH—$(CH_2)_7$—$CH_3$

Esterification reactions of GB are carried out with saturated or unsaturated fatty alcohols (from capric to stearic and oleic alcohols) at 130° C., in the presence of methane sulfonic acid and under reduced pressure in order to eliminate water formed during the process.

In the case of the $C_{18:0}$ stearic derivative, the optimal conditions correspond to one equivalent (0.213 mole, 25 g) of GB, 1.2 equivalent (0.256 mole, 69.3 g) of stearic alcohol and 2.6 equivalent (0.55 mole, 36 ml) of MSA. The reaction mixture is gradually heated for 7 hours to 130° C. under reduced pressure (50 mbar) to remove water formed during the reaction. It is noteworthy that treatment of the mixtures with diethyl ether (weight ratio: 1a/ROH/MSA/GB=70/15/5/10) or n-butanol (weight ratio: 1a/ROH/MSA=70/25/5) led to the total or nearly quantitative removal of residual GB and MSA. The corresponding yield of the ester after treatment is greater than 70%. Table 4 below sets forth the composition of GB stearic ester crude mixture obtained by NMR analysis. Direct flash chromatography of the crude mixture was used to obtain the surfactant with high purity, i.e., >95%.

In the case of the $C_{18:1}$ oleic derivative, the optimal conditions correspond to a GB/ROH/MSA ratio of 1/1.4/2.5. These optimal conditions correspond to one equivalent (0.256 mole, 30 g) of GB, 1.4 equivalent (0.359 mole, 137.5 g) of oleic alcohol and 2.5 equivalent (0.64 mole, 41.54 ml) of MSA. The reaction mixture was stirred under reduced pressure (50 mbar) for 7 hours. The composition of the GB oleic ester crude mixture was obtained by NMR analysis and is set forth in Table 4 below. Direct flash chromatography of the crude mixture was used to isolate the surfactant with a high purity (>95%).

In the case of the myristic/lauric ester $C_{18:0}/C_{12:0}$, the optimal conditions for this synthesis correspond to one equivalent of GB, 1.2 equivalent of myristic/lauric alcohol, and 2.6 equivalent of MSA. The reaction mixture is gradually heated for 7 hours at 120° C. under a much lower pressure (30 mbar) to remove water formed during the reaction. The pressure is gradually reduced from 60 to 30 mbar. The composition of GB myristic/lauric ester crude mixture was obtained by NMR analysis and is set forth in Table 4 below.

While not required, the surfactant crude mixture can be purified by the following described procedure. Neutralization of MSA used in excess with an aqueous $NaHCO_3$ solution followed by the addition of diethyl ether in which myristic/lauric alcohol in the last example, is soluble. The layers are separated and the aqueous layer was extracted with n-butanol/ethylacetate. After concentration to dryness and recrystallation, the pure ester is isolated as a white solid.

The preparation and purification of betainyl amino alkyl methane sulfonates (GB amide derivatives) is now described. GB amides were prepared following a "one-pot two step" procedure. First, one equivalent of GB is reacted with 2.6 equivalent of n-butanol in the presence of 1.1 equivalent of MSA as catalyst at 130° C. for 4 hours. The solvent was distilled out during heating (Dean-Stark apparatus). After cooling, the short butyl chain is replaced by a longer chain in a base-catalyzed aminolysis reaction of the butyl ester using fatty amines ($C_{12}$ lauric amine, $C_{14}$ myristic amine, $C_{16}$ hexadecyl amine, $C_{18:0}$ stearic amine, and $C_{18:1}$ oleic amine). The reaction is then carried out under reduced pressure (50 mbar) at 130° C. in order to eliminate the butanol formed during the process.

The pathway for the one-pot two step GB amide preparation is as follows using for illustrative purposes the production of betainyl amino octadecane methane sulfonate ($C_{18}$ stearic GB amide) and (Z)-betainyl amino octadec-9-ene methane sulfonate (C18:1 oleic GB amide):

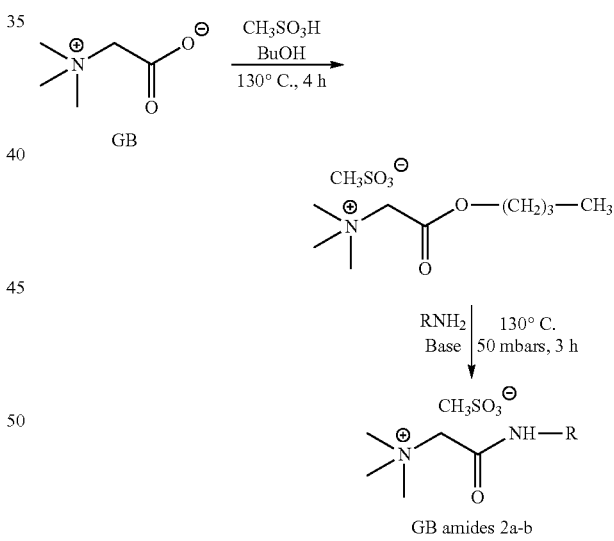

2a: R = $(CH_3)_{17}$—$CH_3$
2b: R = $(H_2C)_8$—CH═CH—$(CH_2)_7$—$CH_3$

This two-stage process includes the recycling of butanol used both as reagent and solvent in this reaction. The addition of an organic base triethanolamine (TEA) or dibutylamine (DBA) into the reaction mixture allows the neutralization of the excess MSA, thus inhibiting the partial protonation of the fatty amine. The crude mixture corresponds to the weight ratio of oleic amine salt/oleic amine/GB=59/34/<1/6. Compound 2b results from flash chromatography of the crude one.

For GB stearic amide ($C_{18:0}$), optimal conditions correspond to a GB/MSA/octadecylamine ratio of 1/1.1/1.2. NMR analysis was used to obtain the crude mixture composition and is set forth in Table 3 below. The crude mixture was purified by precipitation in ethanol yielding to the GB stearic amide partly purified having a weight ratio of stearic amide/stearic amine salts of 60/40 as set forth in Table 3 below. Direct flash chromatography gave a pure stearic amide.

For GB oleic amide ($C_{18:1}$), the optimal conditions correspond to a GB/MSA/oleylamine ratio of 1/1.1/1.2. The crude mixture composition was determined by NMR analysis and is set forth in Table 3 below. Pure oleic amide was provided by direct flash chromatography.

Other betainylaminoalkane methane sulfonates, e.g., GB lauric ($C_{12:0}$), GB myristic ($C_{14:0}$) and GB palmitic ($C_{16:0}$), are synthesized using the same pathway as set for stearic amide. The crude mixture composition of these were also determined by NMR analysis and are set forth in Table 3 below.

DETAILED DESCRIPTION

The production of alkyl(ene) betainate methane sulfonates and betainyl amino alkyl(ene) methane sulfonates is described.

The preparation of and purification of alkyl betainate methane sulfonates (GB ester derivatives) follows a pathway for the esterification reaction of GB as follows:

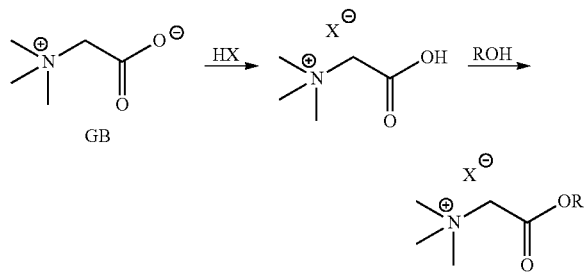

Acid-catalyzed esterification reaction between GB and fatty alcohols proceeds in one-step via the in situ protonation of the carboxylate function. This involves the use of only environmentally friendly raw materials under solvent-free conditions, wherein "solvent-free conditions" refers to the absence during reaction of any compound which functions as a solvent.

The use of methane sulfonic acid (MSA), as the acid for protonation of the carboxylate function is also beneficial in providing a green route to obtain GB esters. MSA is part of the natural sulfur cycle and, therefore, MSA is natural and readily biodegradable. MSA is an easy-to-handle liquid, usually recyclable and less aggressive than common organic acids which are typically used, such as hydrochloric, sulfuric or hydrofluoric acid.

An example of the one-step process of preparing of GB esters, using MSA as catalyst is as described in U.S. Pat. Nos. 7,981,856 and 7,829,521 (which are each incorporated herein by reference) and is illustrated for octadecyl betainate methane sulfonate ($C_{18:0}$ stearic GB ester) and (Z)-octadec-9-enyl betainate methane sulfonate [GB Oleic ester ($C_{18:1}$)] as follows:

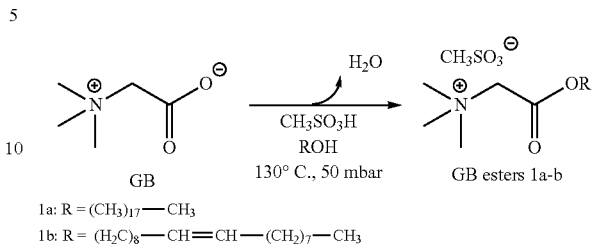

1a: $R = (CH_3)_{17}-CH_3$
1b: $R = (H_2C)_8-CH=CH-(CH_2)_7-CH_3$

Esterification reactions of GB are carried out with saturated or unsaturated fatty alcohols (from capric to stearic and oleic alcohols) at 130° C., in the presence of methane sulfonic acid and under reduced pressure, in order to eliminate water formed during the process.

In the case of the $C_{18:0}$ stearic derivative, the optimal conditions correspond to one equivalent (0.213 mole, 25 g) of GB, 1.2 equivalent (0.256 mole, 69.3 g) of stearic alcohol and 2.6 equivalent (0.55 mole, 36 ml) of MSA. The reaction mixture is gradually heated for 7 hours to 130° C. under reduced pressure (50 mbar) to remove water formed during the reaction. Another advantage of the method of the invention is that treatment of the mixtures with diethyl ether (weight ratio: 1a/ROH/MSA/GB=70/15/5/10) or n-butanol (weight ratio: 1a/ROH/MSA=70/25/5) led to the total or nearly quantitative removal of residual GB and MSA. The corresponding yield of the ester after treatment is greater than 70%.

In the case of the $C_{18:1}$ oleic derivative, the optimal conditions correspond to a GB/ROH/MSA ratio of 1/1.4/2.5. These optimal conditions correspond to one equivalent (0.256 mole, 30 g) of GB, 1.4 equivalent (0.359 mole, 137.5 g) of oleic alcohol and 2.5 equivalent (0.64 mole, 41.54 ml) of MSA. The reaction mixture was stirred under reduced pressure (50 mbar) for 7 hours. Direct flash chromatography of the crude mixture was used to isolate the surfactant with a high purity (>95%).

In the case of the myristic/lauric ester $C_{14:0}/C_{12:0}$, the optimal conditions for this synthesis correspond to one equivalent of GB, 1.2 equivalent of myristic/lauric alcohol, and 2.6 equivalent of MSA. The reaction mixture is gradually heated for 7 hours at 120° C. under a much lower pressure (30 mbar) to remove water formed during the reaction. The pressure is gradually reduced from 60 to 30 mbar. The composition of GB myristic/lauric ester crude mixture was obtained.

While not required, the surfactant crude mixture can be purified by the following described procedure. Neutralization of MSA used in excess with an aqueous $NaHCO_3$ solution followed by the addition of diethyl ether in which myristic/lauric alcohol in the last example, is soluble. The layers are separated and the aqueous layer was extracted with n-butanol/ethylacetate. After concentration to dryness and recrystallation, the pure ester is isolated as a white solid.

The preparation and purification of betainyl amino alkyl methane sulfonates (GB amide derivatives) is now described. GB amides were prepared by a "one-pot two step" procedure. First, one equivalent GB is reacted with 2.6 equivalent n-butanol in the presence of 1.1 equivalent of MSA as catalyst at 130° C. for 4 hours. The solvent was distilled out during heating (Dean-Stark apparatus). After cooling, the short butyl chain is replaced by a longer chain in a base-catalyzed aminolysis reaction of the butyl ester using fatty amines ($C_{12}$ lauric amine, $C_{14}$ myristic amine, $C_{16}$ hexadecyl amine, $C_{18:0}$ stearic amine and $C_{18:1}$ oleic amine). The reaction is then carried out under reduced pressure (50 mbar) at 130° C. in order to eliminate the butanol formed during the process.

The pathway for the one-pot two step amide preparation is as follows using for illustrative purposes the synthesis of betainyl amino octadecane methane sulfonate ($C_{18}$ stearic GM amide) and (z)-betainyl amino octadec9-ene methane sulfonate ($C_{18:1}$ oleic GB amide):

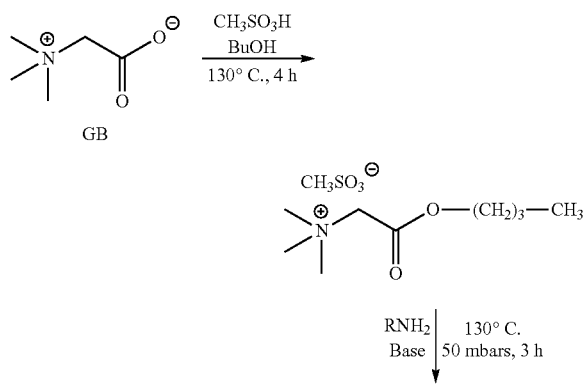

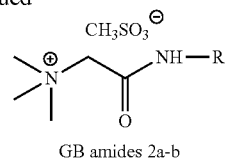

2a: R = $(CH_3)_{17}$—$CH_3$
2b: R = $(H_2C)_8$—CH=CH—$(CH_2)_7$—$CH_3$

GB amides 2a-b

This two-stage process includes the recycling of butanol used both as reagent and solvent in this reaction. The addition of an organic base triethanolamine (TEA) or dibutylamine (DBA) into the reaction mixture allows the neutralization of the excess MSA, thus inhibiting the partial protonation of the fatty amine. The crude mixture corresponds to the weight ratio of oleic amine salt/oleic amine/GB=59/34/<1/6. Compound 2b results from flash chromatography of the crude one.

For GB stearic amide ($C_{18:0}$), optimal conditions correspond to a GB/MSA/octadecylamine ratio of 1/1.1/1.2. NMR analysis was used to obtain the crude mixture composition and is set forth in Table 3 below. The crude mixture was purified by precipitation in ethanol yielding to the GB stearic amide partly purified having a weight ratio of stearic amide/stearic amine salts of 60/40.

For GB oleic amide ($C_{18:1}$), the optimal conditions correspond to a GB/MSA/oleylamine ratio of 1/1.1/1.2.

Other betainylaminoalkane methane sulfonates, e.g., GB lauric ($C_{12:0}$), GB myristic ($C_{14:0}$) and GB palmitic ($C_{16:0}$), are synthesized using the same pathway as set for stearic amide.

Table 1 below sets forth examples of alkyl betainate methane sulfonates obtainable from the above-described preparation process which are useful as surfactants as described herein.

TABLE 1

| Chemical Compounds | Acronyms As Used Herein |
|---|---|
| Octadecyl betainate methane sulfonate, crude | GB Stearic ester ($C_{18:0}$) crude |
| Octadecyl betainate methane sulfonate, pure | GB Stearic ester ($C_{18:0}$) pure |
| (Z)-Octadec-9-enylbetainate methane sulfonate, crude | GB Oleic ester ($C_{18:1}$) crude |
| (Z)-Octadec-9-enylbetainate methane sulfonate, pure | GB Oleic ester ($C_{18:1}$) pure |
| Decyl betainate and dodecyl betainate methane sulfonate, crude | GB Capric/Lauric ($C_{10}/C_{12}$) ester crude |
| Dodecyl/tetradecyl betainate methane sulfonate, crude | GB Lauric/Myristic ($C_{12}/C_{14}$) ester crude |
| Dodecyl/tetradecyl betainate methane sulfonate, pure | GB Lauric/Myristic ($C_{12}/C_{14}$) ester pure |

Table 2 below sets forth examples of betainyl amino alkyl methane sulfonates obtainable from the above-described preparation process which are useful as surfactants as described herein.

TABLE 2

| Chemical Compounds | Acronyms As Used Herein |
|---|---|
| Betainyl ammo octadecane methane sulfonate, crude | GB Stearic amide ($C_{18:0}$) crude |
| Betainyl amino octadecane methane sulfonate, semi-pure | GB Stearic amide ($C_{18:0}$) semi-pure |
| Betainyl amino octadecane methane sulfonate, pure | GB Stearic amide ($C_{18:0}$) pure |
| (Z)-betainyl amino octadec-9-ene methane sulfonate, crude | GB Oleic amide ($C_{18:1}$) crude |
| (Z)-betainyl amino octadec-9-ene methane sulfonate, pure | GB Oleic amide $C_{18:1}$) pure |
| Betainyl amino hexadecane methane sulfonate, crude | GB Palmitic amide $C_{16}$ crude |
| Betainyl amino hexadecane methane sulfonate, pure | GB Palmitic amide $C_{16}$ pure |
| Betainyl amino tetradecane methane sulfonate, crude | GB Myristic amide $C_{14}$ crude |
| Betainyl amino tetradecane methane sulfonate, pure | GB Myristic amide $C_{14}$ pure |
| Betainyl amino dodecane methane sulfonate, pure | GB Lauric amide $C_{12}$ pure |
| Betainyl amino dodecane methane sulfonate, crude | GB Lauric amide $C_{12}$ crude |

Table 3 below sets forth composition components for surfactants based on betainyl amino alkyl(ene) methane sulfonates as within the invention. The composition components were obtained by NMR analysis. Direct flash chromatography of the crude mixture was used to isolate the surfactant with a high purity (i.e., >95%).

TABLE 3

| Surfactants | Composition | Crude | Semi-Pure Wt. % | Pure |
|---|---|---|---|---|
| (Z)-betainyl amino octadec-9-ene methane sulfonate [GB Oleic amide ($C_{18:1}$)] | Oleic amide | 68 | | ≥99 |
| | Oleic ammonium salts | 27 | | |
| | Oleic amine | 0 | | |
| | Glycine Betaine | 5 | | |
| Betainyl amino octadecane methane sulfonate [GB Stearic amide ($C_{18:0}$)] | Stearic amide | 59 | 62 | ≥99 |
| | Stearic ammonium salts | 37 | 38 | |
| | Stearic amine | 0 | 0 | |
| | Glycine Betaine | 4 | 0 | |
| Betainyl amino hexadecane methane sulfonate [GB Palmitic amide $C_{16}$] | Palmitic amide | 64 | | ≥99 |
| | Palmitic ammonium salts | 32 | | |
| | Palmitic amine | 0 | | |
| | Glycine Betaine | 4 | | |
| Betainyl amino tetradecane methane sulfonate [GB Myristic amide $C_{14}$] | Myristic amide | 67 | | ≥99 |
| | Myristic ammonium salts | 28 | | |
| | Myristic amine | 0 | | |
| | Glycine Betaine | 5 | | |
| Betainyl amino dodecane methane sulfonate [GB Lauric amide $C_{12}$] | Lauric amide | 68 | | ≥99 |
| | Lauric ammonium salts | 29 | | |
| | Lauric amine | 0 | | |
| | Glycine Betaine | 3 | | |

Table 3 also provides the weight percentage of the components of the crude mixture as obtained and also as following purification.

Table 4 below sets forth the composition components for surfactants based on alkyl(ene) betaine methane sulfonates within the invention. The composition components were obtained by NMR analysis. Direct flash chromatography of the crude mixture was used to isolate the surfactant within a high purity (i.e., >95%).

TABLE 4

| Surfactants | Composition | Crude Wt. % | Pure |
|---|---|---|---|
| Octadecyl Betainate methane sulfonate [GB Stearic ester ($C_{18:0}$)] | Stearic ester | 58 | ≥99 |
| | Stearic alcohol | 13 | |
| | Methyl sulfonic acid | 25 | |
| | Glycine Betaine | 4 | |
| (Z)-Octadec-9-enyl betainate methane sulfonate [GB Oleic ester ($C_{18:1}$)] | Oleic ester | 47 | ≥99 |
| | Oleic alcohol | 33 | |
| | Methyl sulfonic acid | 17 | |
| | Glycine Betaine | 3 | |
| Tetradecyl/dodecyl Betainate methane sulfonate [GB Myristic/Lauric ester $C_{14}/C_{12}$] | Myristic/Lauric ester | 69 | ≥99 |
| | Myristic/Lauric alcohol | 3 | |
| | Methyl sulfonic acid | 28 | |
| | Glycine Betaine | 0 | |

Table 4 also provides the weight percentage of the components of the crude mixture as obtained and also as following purification.

In traditional betaines, the alkyl chain length is on the nitrogen side structurally. In the compounds of the invention, the alkyl chain length is provided on the carboxylic side structurally. The compounds of the invention also are not synthetically prepared, but rather are prepared from a natural source. A "natural source" is understood to mean a renewable sustainable source, such as a plant source, e.g., sugar beets. Synthetically prepared betaines do not provide for the same crude mixture as obtained when preparing the betaine from a natural source such as sugar beets. Different properties are present based on the different compounds present in the crude mixture obtained from the sugar beets, such as surface properties, wetting, solubilization, spreading, emulsification, foaming ability, gelling, thickening, rheology modifier, adhesion and anti-microbial. It has also been found that different properties are different as between the crude mixture, such crude mixture semi-purified, and such crude mixture substantially or completely purified. These differences are generally ones of degree as to certain properties, and more particularly are wettability, water solubility, emulsifying ability, anti-microbial efficacy, gelling, and thickening.

The crude mixture is a cocktail of compounds. When starting from a natural source, such as sugar beets, one is starting with a different mixture as compared to a synthesis route. In preparation of the GB ester and GB derivatives of the invention, obtained compounds in the crude mixture are identified as well as the different properties associated therewith. By modifying the chain length of the GB ester or GB amide derivatives and manipulating the contents of the crude mixture or blending different chain lengths, the provision or enhancement of certain properties are obtained and, thus, improved surfactants suitable for certain particular product uses can be provided. The crude mixture has synergistic effects. More specifically, preferred chain lengths for the alkyl or alkylene substituent are from $C_8$ to $C_{22}$ carbon atoms. Short chain lengths, i.e., $C_{8-16}$, provide better surfactants and wetting agents, as well as being more water soluble. Long chain lengths, i.e., $C_{18-22}$, provide better emulsification, and so provide good oil cleaning properties. Longer chain lengths of $C_{18-22}$ are even more preferred for forming gels and emulsification. Properties affected by the chain length of the alkyl(ene) substituent of the GB ester and GB amide derivatives of the invention are solubility, micellization, wettability, solubilization, emulsifying efficiency, viscosity, gelling, and thickening. A wide range of chain length is useful depending on the application of the compounds. Normally, surface properties vary when the hydrophobic chain length increases, since the HLB value changes due to less affinity for water. In such case, the change is not so dramatic because of the good solubility of the glycine betaine. The oleic is as good a wetter as the shorter chain. Although it may emulsify oil better, the stearic is less soluble than the oleic due to the saturation.

Another advantage of the structure of the GB ester and GB amide derivatives of the invention prepared from natural sources over synthesized betaine derivatives as known in the art are that the inventive derivatives are provided with an hydrocarbon chain length attached to the carboxylate group which makes the surfactant compound cleavable, i.e., the GB ester and GB amide structures can revert back to the original sugar and alcohol which results in the surfactants being 100% biodegradable.

Surface properties of betainyl amino alkyl(ene) methane sulfonates and alkyl(ene) betainate methane sulfonate surfactants are set forth below in Table 5. Table 5 shows the effects of the hydrocarbon chain length on the surface properties of crude and pure betainyl amino alkyl(ene) methane sulfonate and alkyl(ene) betainate methane sulfonate surfactants. Comparative examples are provided by the GLUCOPON surfactants (commercially available from BASF, formerly known as Cognis) which are alkyl polyglucosides having a carbon length as indicated.

TABLE 5

| Hydrocarbon chain and Benchmarks | CMC* (mol/l) (T = 24° C.) | | Surface Tension @ CMC (mN/m) | |
|---|---|---|---|---|
| | Crude | Pure | Crude | Pure |
| GB Oleic amide | $1.13\ 10^{-4}$ | $1.02\ 10^{-4}$ | 30 | 36 |
| GB Stearic amide | $2.48\ 10^{-4}$ | $2.4\ 10^{-4}$ | 35 | 39 |
| GB Palmitic amide | $2.5\ 10^{-4}$ | $3.39\ 10^{-4}$ | 33 | 37 |
| GB Myristic amide | $6.15\ 10^{-4}$ | $1.02\ 10^{-3}$ | 32 | 38 |
| GB Lauric amide | $1.94\ 10^{-3}$ | $1.2\ 10^{-4}$ | 25 | 38 |
| GB Ester C12 | | | 27 | 38 |
| GB Ester C12/C14 | $5.7\ 10^{-3}$ | $1\ 10^{-3}$ | 24 | 34 |
| GB Ester C18 | $1.68\ 10^{-4}$ | $1.61\ 10^{-4}$ | 30 | 38 |
| GLUCOPON 600, C12-C14 | $7.25\ 10^{-5}$ | | 29 | |
| GLUCOPON 650, C8-C14 | $1.83\ 10^{-4}$ | | 28 | |
| GLUCOPON 425N, C8-C16 | | | 29.7 | |
| GLUCOPON 215, C8-C10 | $6.17\ 10^{-4}$ | | 35 | |
| GENAPOL LA 050 C12/C14 fatty alcohol w/5 EO | | | 27 | |
| GENAPOL LA 090 C12/C14 fatty alcohol w/9 EO | | | 32 | |
| GENAPOL UD 050 C11 oxoalcohol ethoxylate w/5 EO | | | 27 | |
| GENAPOL XO 080 C13 oxoalcohol w/8 EO | | | 27 | |

CMC = Critical Micelle Concentration.

The efficiency of the GB ester and amide derivative surfactants of the invention to emulsify oils, is shown in Tables 6 and 7 and description below with regard to the hydrocarbon group present in the GB ester or GB amide.

TABLE 6

Effect of hydrocarbon groups on the ability of GB surfactants in emulsifying sunflower oil in water

| Surfactants | IFT (mN/m) | |
|---|---|---|
| | Crude | Purified |
| GB Stearic amide | 1.3 | 5.2 |
| GB Oleic amide | 4.2 | 5.5 |
| GB $C_{12}/C_{14}$ Ester | 12.3 | 13.5 |

IFT = Interfacial Tension

TABLE 7

Dynamic Interfacial Tensions of GB Surfactants Against Sunflower Oil @ 0.1% w/w

| Surfactants | IFT (mN/m) |
|---|---|
| GB Lauric Amide, crude | 0.84 |
| GB Palmitic Amide, crude | 0.18 |
| GB Stearic $C_{18:0}$ Amide, crude | 0.65 |
| GB Oleic $C_{18:1}$ Amide, crude | 0.66 |
| GB C12/14 Ester, crude | 4.64 |
| GLUCOPON 215, C8-C10 | 6.62 |
| GLUCOPON 650, C8-C14 | 3.06 |
| GLUCOPON 650, C8-C14 | 1.05 |
| BTC 2125M (n-Alkyl Dimethyl Benzyl Ammonium Chloride (and) n-Alkyl Dimethyl Ethylbenzyl Ammonium Chloride) | 0.92 |

In this testing sunflower oil was emulsified at a neutral pH, stored and analyzed at 25° C. and at 37° C. Oil droplets having a mean diameter of 220 to 260 mm and a narrow size distribution were observed. The emulsion ageing was also followed by photodensitometry, using a flat scanner. GB derivative solutions exhibited emulsifying efficiency at acid, neutral and basic pHs against different types of oil phases, from essential oils, mineral oil and vegetables oils to animal oils and soils, as well as insoluble fragrance and pesticide oils. Due to their ability to solubilize or emulsify a variety of oils, the GB ester and GB amide surfactants allow solubilization and control release of actives, e.g., fragrances, herbicides and pesticides. Surface and interfacial properties of the GB ester and amide derivatives of the invention are comparable to or better than conventional synthesized cationic surfactants, such as quaternary ammonium compounds (QUATs).

In addition to their ability to emulsify polar and non-polar oils, such also form microemulsions spontaneously with GB as emulsifying agents. Upon optimum solubilization of sunflower oil in water, with cetyl trimethyl ammonium bromide (CTAB) used as a reference point (control), a 2-phase system is obtained and not a microemulsion. This was tested using Winsor III microemulsions (i.e., a surfactant rich middle phase which coexists with both water (lower) and oil (upper) surfactant-poor phases) stabilized with GB stearic amide, GB oleic amide, and GB myristic/lauric ester. Each provided three distinct separate layers.

As low as 1 g of surfactants has been determined to lead to the formation of optimum solubilization, i.e., Winsor III microemulsions. GB surfactants produce oil droplets with a particle size smaller than 100 nm and narrow size distribution not exceeding 0.10.

Additionally, the GB derivatives are effective adjuvants in agricultural formulations due to their very low surface and interfacial tensions that enable the formation of very fine particles in spray and aerosol compositions, and excellent and fast wetting of leaf structures.

The surfactants of the invention also have foaming ability. This foaming ability is able to be effectively manipulated, i.e., foaming density increased, based on hydrocarbon chain length. Table 8 below shows the effects of hydrocarbon chain lengths on the foaming behavior of certain GB amide and GB ester derivatives.

TABLE 8

Foamability of GB surfactants compared to alternative surfactants Concentration at CMC, Flow rate: 14 l/min

| Surfactants | Time t: the time to fill 2 liters | Density (g/l) |
|---|---|---|
| Stearic amide, crude | 29 min. | 16 |
| Stearic amide, semi- pure | 9 min., 53 sec. | 23 |
| Oleic amide, crude | 1 min. 22 sec. | 17 |
| Oleic amide, pure | 85 sec. | 18 |
| Palmitic amide, crude | 3 min., 57 sec. | 18 |
| Lauric amide, crude | 3 min., 17 sec. | 22 |
| Ester C12/C14, crude | 56 sec. | 24 |
| Ester C12/C14, pure | 3 min., 59 sec. | 21 |
| BTC 2125M | 1 min., 13 sec. | 16 |
| GLUCOPON 600, C12-C14 | >33 min., the beaker is not filled | — |
| GLUCOPON 650, C8-C14 | >40 min., the beaker is not filled | — |

The GB ester and GB amide derivative surfactants also provide good cleaning performance and have good wetting properties. Cleaning performance and wetting properties are set forth in Table 9 below with respect to certain GB ester and GB amide derivative surfactants of the invention and certain comparative examples, i.e., the conventional surfactants of an alkyl polyglucoside (APG) GLUCOPON 425N manufactured by BASF (formerly known as Cognis) and a quaternary ammonium BTC 2125M manufactured by Stepan Company.

TABLE 9

| Surfactants | Conc. % (w/w) | Cleaning Performance (time to remove soils) (sec) | | | Wetting Properties Contact Angles on treated substrates (°) | | |
|---|---|---|---|---|---|---|---|
| | | Greasy Kitchen | Interior | Glass | Enamel Tiles | Kitchen Soil | Soap Scum |
| GB Oleic C18:1 Amide | 1 | 15 | 10 | 22.6 | 27.6 | 46.4 | 31.1 |
| GB Oleic C18:1 Amide | 3 | 15 | 10 | 18.8 | 26.8 | 38.1 | 31.3 |
| GB Stearic-C18:0 Amide | 1 | 10 | 10 | 23.1 | 35.4 | 39.7 | 31.6 |
| GB Stearic C18:0 Amide | 3 | 10 | 10 | 19.4 | 27.1 | 34.6 | 34.3 |
| GB Myristic/Lauric $C_{14}/C_{12}$ ester | 1 | 20 | 10 | 16.9 | 25.9 | 43.1 | 22.1 |
| GB Myristic/Lauric $C_{14}/C_{12}$ ester | 3 | 20 | 10 | 13.4 | 24.1 | 39.6 | 26.1 |
| GLUCOPON APG 425N ($C_8$-$C_{14}$ Alkylpolyglucoside) | 1 | >120 | 10 | 8.1 | 21.9 | 51.5 | 19.8 |
| BTC2125M | 1 | >120 | 10 | 30.6 | 29.1 | 59.6 | 58.4 |

To further illustrate the efficiency of the GB ester and GB amide derivative surfactants of the invention in solubilizing kitchen soils, and the difference between crude and purified forms of the surfactants, additional cleaning performance data is set forth in Table 10 and is compared against conventional surfactants, i.e., various nonionic APG GLUCOPON surfactants, an amphoteric surfactant REWOCID WK30 manufactured by Evonik Industries, and a cationic quaternary ammonium surfactant BTC 2125.

TABLE 10

| | Percent of Soil Solubilized by GB surfactants and Benchmark Contact time (sec) | | | | | |
|---|---|---|---|---|---|---|
| | 20 | | 30 | | 60 | |
| | crude | purif. | crude | purif. | crude | purif. |
| Inventive Surfactants | | | | | | |
| Oleic amide | 20.0 | | 24.5 | | 51.1 | |
| Stearic amide | 12.0 | 12.3* | 38.8 | 21.6* | 54.2 | 49.5* |
| Palmitic amide | 44 | | 47 | | 55 | |
| Myristic amide | 48 | | 44 | | 76 | |
| Lauric amide | 22.0 | | 46.0 | | 77.0 | |
| Ester $C_{12}/C_{14}$ | 22.8 | 18.2 | 30.2 | 40.2 | 67.9 | 42.7 |
| Comparative Surfactants | | | | | | |
| GLUCOPON 600, $C_{12}$-$C_{14}$ APG | 38.5 | | 55.0 | | 76.4 | |
| GLUCOPON 650, $C_8$-$C_{14}$ APG | 18.6 | | 17.4 | | 45.1 | |
| GLUCOPON 215, $C_8$-$C_{10}$ APG | 13.5 | | 35.7 | | 40.4 | |
| Rewocid WK30 (Amines, N-C10-16-Alkyl trimethylenedi,-reaction products with chloro acetic acid) | 16.2 | | 39.2 | | 40.9 | |
| BTC 2125 (Alkyl Dimethyl Benzyl & Benzyl/Ethyl Quaternary Ammonium Chlorides) | 22.7 | | 30.0 | | 45.0 | |

*Semi-purified

NOTE:
Comparative surfactants were used as commercially purchased and were not in "crude" or "purified" state as with inventive surfactants.

Tables 11 and 12 below further show the cleaning performance of GB ester and GB amide derivative surfactants of the invention as compared to commercially available surfactants by the amount of soil solubilized by the respective surfactants.

TABLE 11

Cleaning Performance of Betainyl amino Alkyl (ene) Methane Sulfonate and Alkyl (ene) Betainate Methane Sulfonate Surfactants compared to commercially available quaternary ammonium salts (BTC 2125M) after 20 seconds contact time

| | Bathroom Soap Scum Solubilized (%) | |
|---|---|---|
| Aqueous Solutions of Surfactants | Crude | Pure |
| GB Oleic ($C_{18:1}$) amide | 94 | |
| GB Stearic ($C_{18:0}$) amide | 66 | 35 |
| GB Lauric ($C_{12}$) amide | 55 | |
| GB Ester $C_{12}/C_{14}$ | 80 | 69 |
| BTC 2125M | 13 | |

TABLE 12

Cleaning Performance (% Solubilized) of Betainyl amino Alkyl (ene) Methane Sulfonate and Alkyl (ene) Betainate Methane Sulfonate Surfactants compared to Benchmark surfactants

| | Contact Time (sec) | | | | | |
|---|---|---|---|---|---|---|
| | 30 | | 60 | | 120 | |
| | Crude | Pure | Crude | Pure | Crude | Pure |
| Oleic amide | 76 | | 80 | | 83 | |
| Stearic amide | 80 | 78* | 64 | 66* | 86 | 85* |
| Palmitic amide | 75 | | 76 | | 84 | |
| Myristic amide | 83 | | 84 | | 80 | |
| Ester C12/C14 | 70 | 80 | 74 | 84 | 82 | 84 |
| Lauric amide | 80 | | 74 | | 82 | |
| Benchmark | | | | | | |
| GLUCOPON 600, $C_{12}$-$C_{14}$ | 82 | | 84 | | 85 | |
| GLUCOPON 650, $C_8$-$C_{14}$ | 82 | | 84 | | 86 | |

TABLE 12-continued

Cleaning Performance (% Solubilized) of Betainyl amino Alkyl (ene) Methane Sulfonate and Alkyl (ene) Betainate Methane Sulfonate Surfactants compared to Benchmark surfactants

| | Contact Time (sec) | | | | | |
|---|---|---|---|---|---|---|
| | 30 | | 60 | | 120 | |
| | Crude | Pure | Crude | Pure | Crude | Pure |
| GLUCOPON 215, $C_8$-$C_{10}$ | 72 | | 82 | | 89 | |
| REWOCID WK30 | 80 | | 65 | | 80 | |
| BTC 2125M | 70 | | 68 | | 89 | |

*= Semi-pure

NOTE:
Benchmark surfactants were used as commercially purchased and were not in "crude" or "pure" form as with the inventive surfactants.

Cleaning compositions including surfactants of the invention are generally as follows:

| Ingredient | Concentration (% w/w) |
|---|---|
| Water | balance to 100 |
| GB ester or GB amide derivative(s) | 0.5 to 3 |
| Chelator/pH adjuster | 0 to 0.5 |
| Adjuvant(s) (e.g. fragrance) | 0 to 1.5 |

Compounds suitable for use as chelator(s) or pH adjuster(s) are as generally known in the art and include, for example, carboxylic acids or their salts, such as lactic acid, citric acid, itaconic acid, tartaric acid, gluconate, glucarate; alkali metal hydroxides such as sodium hydroxide, and the like.

Adjuvant(s) suitable for inclusion are as generally known in the art and include, for example, surfactants, wetting agents, solubilizing agents, thickening agents used in combination with pesticides, herbicides, sprayability and delivery systems to enhance the performance of the products. Conventional aesthetic-providing adjuvants can also be included, e.g., fragrances, colorants, etc.

Table 13 sets forth Examples I-VI cleaning compositions including surfactants of the invention. These composition are utilized in comparative cleaning tests as further described below.

TABLE 13

| Ingredients | Function | Concentration (% w/w) |
|---|---|---|
| Example I | | |
| Deionized Water | Diluent | 93.85 |
| Glycine Betaine $C_{12/14}$ Ester | Surfactant | 3 |
| Lactic Acid | Chelator/pH adjuster | 3 |
| Fragrance | Perfume | 0.15 |
| Example II | | |
| Deionized Water | Diluent | 95.85 |
| Glycine Betaine $C_{12/14}$ Ester | Surfactant | 1 |
| Lactic Acid | Chelator/pH adjuster | 3 |
| Fragrance | Perfume | 0.15 |
| Example III | | |
| Deionized Water | Diluent | 93.85 |
| Glycine Betaine Oleic Amide | Surfactant | 3 |
| Lactic Acid | Chelator/pH adjuster | 3 |
| Fragrance | Perfume | 0.15 |
| Example IV | | |
| Deionized Water | Diluent | 95.85 |
| Glycine Betaine Oleic Amide | Surfactant | 1 |
| Lactic Acid | Chelator/pH adjuster | 3 |
| Fragrance | Perfume | 0.15 |
| Example V | | |
| Deionized Water | Diluent | 95.85 |
| Glycine Betaine Stearic Amide | Surfactant | 1 |
| Lactic Acid | Chelator/pH adjuster | 3 |
| Fragrance | Perfume | 0.15 |
| Example VI | | |
| Deionized Water | Diluent | 95.85 |
| Glycine Betaine Stearic Amide | Surfactant | 3 |
| Lactic Acid | Chelator/pH adjuster | 3 |
| Fragrance | Perfume | 0.15 |

Table 14 sets forth results of tests comparing the soil removed performance of the compositions of Example I-VI as set forth in Table 13 compared to various commercial products. The various properties of the Examples show that the compositions of the invention are better than or comparable to commercial products in cleaning performance. All inventive compositions, including those which are comparable in performance, provide the added advantage of being 100% biodegradable which is an advantage over the commercial products.

TABLE 14

Soil Removal Performance of prototype formulas comprising Betainyl amino Alkyl (ene) Methane Sulfonate and Alkyl (ene) Betainate Methane Sulfonate Surfactants compared to commercial Products

| | pH | Surfactant Conc. % (w/w) | Surface Tension (mN/m) | Contact Angle Enamel (°) | Contact Angle GKS (°) | Contact Angle Soap Scum (°) | Kitchen Soil Removal (sec) | Interior Soil Removal (sec) |
|---|---|---|---|---|---|---|---|---|
| Glass Cleaner | 3.5 | | 26.31 | 8.3 | 16.7 | 21.1 | >20 | 10 |
| Natural Glass Cleaner | 11.09 | | 28.46 | 25.4 | 25.3 | 24.9 | >20 | 10 |
| Bathroom Cleaner | 2.5 | | 27.35 | 8.6 | 30.3 | 11.1 | >20 | 10 |
| Natural Bathroom Cleaner | 2.06 | | 27.59 | 12.1 | 33.9 | 13.9 | >20 | 10 |
| Natural All Purpose Cleaner | 11.46 | | 28.76 | 21.2 | 36.3 | 19.6 | 20 | 10 |
| All Purpose Cleaner | 11.1 | | 26.66 | 8.6 | 12.4 | 21.7 | 10 | 10 |

TABLE 14-continued

Soil Removal Performance of prototype formulas comprising Betainyl amino
Alkyl (ene) Methane Sulfonate and Alkyl (ene) Betainate Methane Sulfonate
Surfactants compared to commercial Products

|  | pH | Surfactant Conc. % (w/w) | Surface Tension (mN/m) | Contact Angle Enamel (°) | Contact Angle GKS (°) | Contact Angle Soap Scum (°) | Kitchen Soil Removal (sec) | Interior Soil Removal (sec) |
|---|---|---|---|---|---|---|---|---|
| All Purpose Anti-Bacterial Cleaner | 10.51 |  | 27.44 | 6.1 | 13.6 | 26.1 | 10 | 10 |
| Example I |  | 3 |  | 19.8 | 38.1 | 17.6 | 20 | 10 |
| Example II |  | 1 |  | 20.2 | 41.3 | 19.1 | 20 | 10 |
| Example III |  | 3 |  | 26.5 | 36.4 | 26.9 | 15 | 10 |
| Example IV |  | 1 |  | 26.9 | 37.5 | 28.6 | 15 | 10 |
| Example V |  | 3 |  | 27.2 | 41.3 | 30.6 |  | 10 |
| Example VI |  | 1 |  | 27.9 | 41.6 | 30.9 |  | 10 |

The betainyl amino alkyl(ene) methane sulfonates and alkyl(ene) betainate methane sulfonates also provide unique gelling and thickening, in itself, including as a crude mixture, and also in combination with sodium chloride.

When used in itself to provide thickening, the GB ester and GB amide derivatives are provided with a long alkyl or alkylene chain length, i.e., from about 14 to 22 carbon atoms, and in a high concentration in order to achieve phase transition, i.e., at least about 30 wt. %. Contrary to conventional thickening agents, GB esters and GB amides of the present invention have the ability to provide thickening at room temperature. Processing that conventionally requires heating and cooling cycles can with the compounds of the invention be achieved without heating. If the process requires a heating step for any reason, the gelling on thickening provided is reversible.

Alternatively, and more beneficially, to provide thickening or gelling, any one of sodium chloride, potassium chloride, magnesium chloride, a natural gum, or a polysaccharide is added in an amount of greater than 0 to about 10 wt. %, preferably about 0.5 to about 8 wt. %, and most preferably about 6 wt. % in combination with the surfactant component which provides a gel without the necessity of heating and cooling steps. Examples of natural gum suitable for use include xanthan gum, and guar gum. Examples of polysaccharides suitable for use include starch, carrageenans (alpha, kappa, iota, etc.), cellulose derivatives, and the like. Based on the alkyl or alkylene chain length provided in the GB ester or GB amide derivatives and whether an ester or an amide derivative is used, different gels for different applications can be provided, e.g., cosmetic, home cleaning, etc. Chain lengths of from 14 to 22 carbon atoms are generally preferred for use in the GB ester or GB amide derivatives. The longer chain lengths provide for greater thickening. GB amide derivatives are preferred as providing for compositions having pH values from neutral to alkaline as compared to the ester derivatives.

Table 15 below illustrates the thickening of GB stearic amine aqueous solution as a function of concentration and time.

TABLE 15

| Surfactant Concentration (% w/w) | Initial Viscosity (cP) | Viscosity after 15 days (cP) |
|---|---|---|
| 1 | 120 | 160 |
| 2 | 160 | 639 |
| 3 | 160 | 807 |

TABLE 15-continued

| Surfactant Concentration (% w/w) | Initial Viscosity (cP) | Viscosity after 15 days (cP) |
|---|---|---|
| 4 | 2259 | 3626 |
| 5 | 3039 | 6079 |
| 6 | 5279 | 8851 |

The examples of Table 15 are compounds present in water alone and, thus, the viscosity continues to change. After a certain point, the viscosity will plateau and not change anymore. If the surfactant is provided at a predetermined concentration, the desired viscosity will be reached right away and not continue to increase due to the stability provided. Thus, generally, as the surfactant concentration increases, so does the initial viscosity. Also over a period of time, the viscosity increases. The viscosity can be controlled to terminate the viscosity increase, i.e., achieve a predetermined viscosity, by adding salts to the composition. Preferred salts are sodium chloride, potassium chloride, magnesium, chloride, and lithium chloride. Another feature of the invention is the ability to combine GB surfactants with natural polysaccharides to form gel and pseudoplastic viscous liquids or gels. Examples of polysaccharides are agar, carregenan, natural gum, pectin, gelatin, starch, cellulose derivatives, cellulose derived from wood pulp fiber, lignin, etc.

Table 16 below illustrates the effect of sodium chloride on the gelling and thickening ability of betainyl amino alkylene) methane sulfonate surfactants.

TABLE 16

| NaCl Concentration | GB Oleic amide crude | | GB Stearic amide crude | |
|---|---|---|---|---|
| (w/w) % | pH | Viscosity | pH | Viscosity |
| 0.0 | 4.99 | 853.1 | 4.72 | 479.9 |
| 0.2 | 5.91 | 1120 | 6.7 | 4159 |
| 0.4 | 5.95 | 2080 | 6.85 | 3039 |
| 0.6 | 5.99 | 2240 | 6.86 | 5439 |
| 0.8 | 5.99 | 2240 | 6.61 | 5900 |
| 1.0 | 5.99 | 2240 | 6.66 | 6879 |

Once the pH plateaus, the viscosity increase no longer changes. The salt content and/or surfactant concentration determine the viscosity obtained. The results of Table 14 keep changing in viscosity based on being present only in water. Once present in a composition at a specific pH and concentration, stability is provided to control and maintain the viscosity obtained. Alternatively, the salt content can be used to control the viscosity level.

A major feature of the compositions of the invention is the ability of the compositions to kill or inhibit the growth of gram positive and gram negative bacteria and fungi. Both GB esters and GB amides of the invention exhibit extremely minimum inhibition concentration (MIC). Furthermore, the compositions that contain these surfactants exhibit high antimicrobial efficacy, requiring only a minimum concentration.

The efficacy of zwitterionic and amphoteric betaines, such as N-alkyl betaine and N-alkyl-N,N-dimethylamine oxide, against Salmonella and E-coli for pharmaceutical, chemotherapeutical, food applications and personal care applications is known in the art. Some examples are illustrated and shown in the following publications: (1) "Antimicrobial Evaluation of N-Alkyl Betaines and N-Alkyl-N,N-Dimethylamine Oxides with Variations in Chain Length", *Antimicrobial Agents Chemother.*, 2000 September, Vol. 44(9): pages 2514-2517", and (2) "Antimicrobial Composition And Methods Of Making And Using Same", U.S. Patent Application Publication No. 2010/0086576 A1. The betaine and amine oxide surfactants described in these publications are amphoteric, comprising both quaternary amine and carboxylic groups.

The cationic glycine betaine with ester and amide linkages of the present invention also exhibit strong efficacy against both gram positive and gram negative bacteria. Their minimum inhibition concentration (MIC) values have been found to be lower than that of amphoteric betaines. Moreover, they exhibit a much lower Critical Micelle Concentration (CMC) and, therefore, have better surfactant properties than conventional amphoteric surfactants.

To illustrate the antimicrobial properties of the surfactants of the invention, the surfactants were tested against the following organisms: (1) *Salmonella*, (2) *Staphylococcus Aureus* and (3) *E. coli* (ATCC 11229).

First is described Minimum Inhibition Concentration (MIC) of green compositions and green surfactants of the invention against *E. coli*. Since all the products are liquid, the solid contents in all samples were measured prior to the determination of the MIC using *E. coli* (ATCC 11229) as a typical Gram-negative bacterium. The MIC method, also called broth dilution, is a popular conventional antimicrobial test used for investigating antimicrobial compounds. Fresh cultured *E. coli* was diluted with Luria-Bertani (LB) broth to 106 CFU/mL. Serial solutions of the test samples with the concentration from 500 to 1.75 ppm, were made by dilution with sterile LB broth. Then, 0.2 ml of *E. coli* (106 CFU/mL) was added to the product/broth solutions, and seeded tubes were incubated at 37° C. for 18 hours. The MIC was interpreted as the lowest concentration that could inhibit the visible growth of bacteria compared with that of the control samples. Accordingly, the original sample had a concentration of 100%. The dilution factor for seven diluted samples was 1/2, 1/4, 1/8, 1/16, 1/32, 1/64 and 1/128. The effective MIC solid content times the dilution factor. Table 17 below shows the growth inhibition (%) of gram negative *Esherichia coli* of different surfactants and dosages using the shaking flask method.

TABLE 17

| Glycine Betaine Fatty Ester or Amide Surfactants | Growth Inhibition (%) | |
|---|---|---|
| Surfactant Concentration (ppm) | 100 | 50 |
| Betainylaminododecane methanesulfonate $C_{12}$ Amide, Crude | 100 | 99 |
| Betainylaminododecane/tetradecanemethanesulfonate $C_{12}/C_{14}$ Ester, Pure | 100 | 96 |
| Betainylaminododecane methanesulfonate $C_{12}/C_{14}$ Ester, Crude | 90 | 76 |
| (Z)-Betainylaminooctadec-9-ene methanesulfonate ($C_{18:1}$) oleic Amide, Crude | 100 | 88 |

* MIC is as the lowest concentration that could inhibit the visible growth of bacteria compared with that of the control samples. The effective MIC value equals to the solid content times dilution factor.

Table 18 shows the minimum inhibition concentration (MIC)* for selected betainyl amino alkyl(ene) methane sulfonate and alkyl(ene) betaine methane sulfonate surfactants.

TABLE 18

| Glycine Betaine Fatty Ester or Amide Surfactants | Effective MIC (ppm) |
|---|---|
| Betainylaminododecane methanesulfonate $C_{12}$ Amide, Crude | 32 |
| Betainylaminododecane/tetradecanemethanesulfonate $C_{12}/C_{14}$ Ester, Pure | 32 |
| Betainylaminododecane methanesulfonate $C_{12}/C_{14}$ Ester, Crude | 32 |
| (Z)-Betainylaminooctadec-9-ene methanesulfonate ($C_{18:1}$) oleic Amide, Crude | 16 |

* MIC is as the lowest concentration that could inhibit the visible growth of bacteria compared with that of the control samples. The effective MIC value equals to the solid content times dilution factor.

Table 19 shows the antimicrobial efficacy of compositions comprising betainyl amino alkyl(ene) methane sulfonate and alkyl(ene) betaine methane sulfonate surfactants against gram positive *staphylococcus aureus* at 5 minutes contact time.

TABLE 19

| Examples | Log Reduction | Percent Reduction |
|---|---|---|
| Aqueous solution of Glycine Betaine $C_{12}/C_{14}$ Ester, Pure | 5.25837 | 99.99944 |
| Aqueous Solution of Glycine Betaine $C_{12}/C_{14}$ Ester, Crude | 2.917614 | 99.87911 |
| Aqueous Solution of Glycine Betaine $C_{12}$ Amide, Crude | 5.3732 | 99.99958 |
| Aqueous Solution of Glycine Betaine $C_{18}$ Amide, Crude | 5.104765 | 99.99921 |
| Example I Bath with $C_{12}/C_{14}$ pure GB Ester, Pure | 4.692969 | 99.99797 |
| Example II Bath with $C_{12}/C_{14}$ crude GB Este, Crude | 4.496774 | 99.99681 |
| Example III Bath with $C_{18:1}$ Oleic GB Ester, Crude | 3.3368 | 99.95395 |
| Example IV Bath with $C_{12}$ crude GB Amide, Crude | 3.311277 | 99.5117 |
| Example V Toilet liquid with $C_{12}/C_{14}$ Ester + citric acid, Crude | 3.26794 | 99.94604 |
| Example VI Toilet liquid with $C_{12}/C_{14}$ + lactic acid, Crude | 4.807776 | 99.99844 |
| Example VII current toilet liquid with APG + lactic acid (control) | 3.71101 | 99.98055 |

The following provides a definition of the surfactant compositions of Examples I-VII above.

Example I

Application Bath Dodecyl/Tetradecylbetainate methanesulfonate Ester $C_{12}/C_{14}$ Pure as surfactant and antimicrobial agent.

Example II

Application Bath Dodecyl/Tetradecylbetainate methanesulfonate Ester $C_{12}/C14$ crude as surfactant and antimicrobial agent.

Example III

Application Bath (Z)-Betainylaminooctadec-9-ene methanesulfonate $C_{mil}$ as surfactant and antimicrobial agent.

Example IV

Application Bath Betainylaminododecane methanesulfonate (C12) Lauric amide Crude mixture as surfactant and antimicrobial agent.

Example V

Application Toilet liquid+citric acid+Dodecyl/Tetradecylbetainate methanesulfonate Ester $C_{12}/C_{14}$ crude, as surfactant and antimicrobial agent. This composition includes synergistic effects of surfactant and citric acid as chelator.

Example VI

Application Toilet Liquid+lactic acid+Dodecyl/Tetradecylbetainate methanesulfonate Ester $C_{12}/C_{14}$ crude as surfactant and antimicrobial agent. This composition provides synergistic effects of surfactant and lactic acid as chelator.

Example VII

Application Toilet liquid+lactic acid+APG: current technology as control.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. A cleaning composition consisting of:
  (A) 0.5 to 3 wt. % of a glycine betaine derivative having a formula:

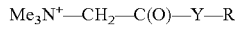

wherein Y is —NH—; and R is a hydrocarbon group having 8 to 22 carbon atoms;
  (B) a chelating agent, wherein the composition contains no more than 3.0 wt. % of the chelating agent;
  (C) 0 to 1.5 wt. % of one or more adjuvants selected from the group consisting of fragrances and colorants;
  (D) greater than 0 and no more than 8 wt. % of a polysaccharide;
  (E) one or more of methanesulfonic acid, glycine betaine and an amine R—NH$_2$ or salt thereof, where R is as defined;
  (F) optionally, a glycine betaine ester having a formula:

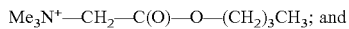

and
  (G) a balance water.

2. The composition of claim 1 wherein the R group is a $C_8$, $C_{10}$, $C_{12}$, $C_{14}$, $C_{16}$ and/or $C_{18}$ alkyl group and/or an oleic group.

3. The composition of claim 2 wherein the composition comprises the R—NH$_2$ compound; and optionally methanesulfonic acid; and optionally glycine betaine.

4. The composition of claim 1 wherein the composition is a thickened liquid.

5. The composition of claim 1 wherein the composition is a gel.

6. The composition of claim 1, wherein the chelating agent is selected from the group consisting of lactic acid, citric acid, tartaric acid, gluconic acid, itaconic acid, glutaric acid, alkali metal salts thereof, and mixtures thereof.

7. The composition of claim 1, wherein the glycine betaine component comprises a glycine betaine derivative in which R is a lauric group and/or a glycine betaine derivative in which R is a myristic group.

8. The composition of claim 1, wherein the R group is a $C_8$-$C_{16}$ hydrocarbon group.

9. The composition of claim 1, wherein the composition comprises a glycine betaine derivative in which the R group is a lauric group.

10. The composition of claim 1, wherein the polysaccharide comprises a natural gum selected from the group consisting of xanthan gum and/or guar gum.

11. The composition of claim 1, wherein the polysaccharide comprises agar, carrageenan, pectin, starch, xanthan gum, guar gum and/or a cellulose derivative.

12. A cleaning composition consisting of:
  (A) 0.5 to 3 wt. % glycine betaine amide having a formula:

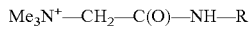

wherein R is a hydrocarbon group having 8 to 22 carbon atoms;
  (B) chelating agent, selected from the group consisting of lactic acid, citric acid, tartaric acid, gluconic acid, itaconic acid, glutaric acid, alkali metal salts thereof, and mixtures thereof;
  (C) polysaccharide, wherein the polysaccharide includes starch and the polysaccharide is present in an amount sufficient to thicken said composition, and the composition contains no more than 8 wt. % of the polysaccharide;
  (D) optionally, one or more adjuvants selected from the group consisting of fragrances and colorants;
  (E) one or more of methanesulfonic acid, glycine betaine and an amine R—NH$_2$ or salt thereof, where R is as defined;

(F) optionally, a glycine betaine ester having a formula:

$MeSO_3^-$ $Me_3N^+—CH_2—C(O)—O—(CH_2)_3CH_3$; and (G) water.

13. The composition of claim 12, wherein the composition comprises a mixture of glycine betaine amides having R groups with 12 carbon atoms and 14 carbon atoms; the chelating agent comprises citric acid; the polysaccharide comprises xanthan gum.

14. The composition of claim 12, wherein the composition is a gel.

15. A cleaning composition consisting of:
(A) 0.5 to 3 wt. % glycine betaine amide having a formula:

$MeSO_3^-$ $Me_3N^+—CH_2—C(O)—NH—R$ wherein R is an aliphatic hydrocarbon group having 8 to 22 carbon atoms;
(B) one or more of an amine R—$NH_2$ or salt thereof, where R is as defined, methanesulfonic acid and glycine betaine;
(C) starch;
(D) lactic acid or an alkali metal salt thereof;
(E) optionally, colorant and/or fragrance;
(F) optionally, a glycine betaine ester having a formula:

$MeSO_3^-$ $Me_3N^+—CH_2—C(O)—O—(CH_2)_3CH_3$; and (G) water.

16. The composition of claim 15, wherein the R group includes a $C_{16}$ and/or $C_{18}$ alkyl group and/or an oleic group.

17. The composition of claim 15, wherein the R group includes a $C_{12}$ and/or $C_{14}$ alkyl group.

18. A cleaning composition consisting of:
(A) 0.5 to 3 wt. % glycine betaine amide having a formula:

$MeSO_3^-$ $Me_3N^+—CH_2—C(O)—NH—R$ wherein R is a hydrocarbon group having 8 to 22 carbon atoms;
(B) a co-surfactant;
(C) optionally, one or more adjuvants selected from the group consisting of fragrances and colorants;
(D) one or more of methanesulfonic acid, glycine betaine and an amine R—$NH_2$ and/or salt thereof, where R is as defined;
(E) optionally, a glycine betaine ester having a formula:

$MeSO_3^-$ $Me_3N^+—CH_2—C(O)—O—(CH_2)_3CH_3$; and (F) water; wherein the cleaning composition is a gel.

19. The composition of claim 18, wherein the glycine betaine amide comprises a compound in which the R group is a lauric group, the R group is a myristic group or a mixture thereof.

20. The composition of claim 19, wherein the composition comprises the R—$NH_2$ compound; and optionally methanesulfonic acid; and optionally glycine betaine.

21. The composition of claim 18, wherein the composition consists of the glycine betaine amide; the co-surfactant; the amine R—$NH_2$ and/or salt thereof; water; optionally, methanesulfonic acid; optionally, glycine betaine; and optionally, fragrance and/or colorant.

22. The composition of claim 18, wherein the R group includes a $C_{16}$ and/or $C_{18}$ alkyl group and/or an oleic group.

23. The composition of claim 18, wherein the R group includes a $C_{12}$ and/or $C_{14}$ alkyl group.

24. The composition of claim 18, wherein R is a hydrocarbon group having 18 to 22 carbon atoms.

25. The composition of claim 18, wherein the R group includes a $C_{18}$ alkyl group.

* * * * *